(12) United States Patent
Bohse et al.

(10) Patent No.: US 7,698,943 B2
(45) Date of Patent: Apr. 20, 2010

(54) METHOD FOR EVALUATING PRESSURE CONTAINERS OF COMPOSITE MATERIALS BY ACOUSTIC EMISSION TESTING

(75) Inventors: Juergen Bohse, Berlin (DE); Georg M. Mair, Grossbeeren (DE)

(73) Assignee: Bam Bundesanstalt Fuer Materialforschung und-Pruefung, Berlin (DE)

( * ) Notice: Subject to any disclaimer, the term of this patent is extended or adjusted under 35 U.S.C. 154(b) by 418 days.

(21) Appl. No.: 11/778,602

(22) Filed: Jul. 16, 2007

(65) Prior Publication Data
US 2008/0302186 A1 Dec. 11, 2008

Related U.S. Application Data

(60) Provisional application No. 60/807,720, filed on Jul. 19, 2006.

(30) Foreign Application Priority Data
Jul. 19, 2006 (DE) .................. 10 2006 033 905

(51) Int. Cl.
*G01N 29/14* (2006.01)
*G01N 37/00* (2006.01)
(52) U.S. Cl. ................ 73/587; 73/37; 73/602; 73/801; 702/82
(58) Field of Classification Search ............ 73/587, 73/37, 49.5, 602, 801, 807; 702/81, 82
See application file for complete search history.

(56) References Cited

U.S. PATENT DOCUMENTS

| 3,545,262 | A | | 12/1970 | Steele et al |
| 3,752,255 | A | * | 8/1973 | Hill et al. ................ 73/596 |
| 4,162,636 | A | * | 7/1979 | Lather et al. ............ 73/638 |
| 4,277,979 | A | * | 7/1981 | Vilkomerson et al. ...... 73/633 |
| 4,469,106 | A | * | 9/1984 | Harui ..................... 600/461 |
| 4,577,487 | A | | 3/1986 | Dooley et al. |
| 5,005,417 | A | * | 4/1991 | Kawasaki et al. .......... 73/593 |
| 5,535,628 | A | * | 7/1996 | Rutherford ............... 73/622 |
| 5,690,110 | A | * | 11/1997 | Tanaka .................... 600/446 |
| 5,814,731 | A | * | 9/1998 | Alexander et al. ......... 73/644 |
| 6,785,616 | B2 | * | 8/2004 | Lung et al. ............... 702/34 |
| 2007/0074573 | A1 | * | 4/2007 | Ester et al. ............... 73/660 |
| 2009/0010285 | A1 | * | 1/2009 | Dubois et al. ............. 372/3 |

FOREIGN PATENT DOCUMENTS

| DE | 19701405 C2 | 7/1998 |
| DE | 102004027804 A1 | 6/2006 |
| EP | 0855684 A2 | 7/1998 |

* cited by examiner

*Primary Examiner*—J M Saint Surin
(74) *Attorney, Agent, or Firm*—Nixon Peabody LLP

(57) ABSTRACT

The invention relates to a method for evaluating pressure containers made of a composite material by acoustic emission testing. The method comprises the steps: (a) determining a sufficient number of internal pressure-dependent acoustic emission characteristics (AE characteristics) of pressure containers from identical production that have been classified as being without defects in predetermined phases of a time-controlled pressure acting upon the pressure container (AE test procedure) with one or more acoustic emission channels (AE channels) using acoustic emission sensors (AE sensors) of a predetermined position (one AE characteristic per AE sensor or AE channel.

10 Claims, 2 Drawing Sheets

METHOD FOR EVALUATING PRESSURE CONTAINERS OF COMPOSITE MATERIALS BY ACOUSTIC EMISSION TESTING

CROSS-REFFERENCE TO RELATED APPLICATIONS

This application claims the benefit of U.S. Provisional Application No. 60/807,720, filed Jul. 19, 2006, and claims priority from German Application No. DE 10 2006 033 905.3, filed Jul. 19, 2006.

The invention relates to (i) a method for evaluating pressure containers (pressure vessels, propellant gas storage devices, other pressure containers with an internal pressure of more than 2 bar) made of a composite material by means of as acoustic emission test method (AE test method), (ii) a data medium or circuit that contains the feature criteria, evaluation criteria or rejection criteria determined in substeps of the method, (iii) an AE test system for performing the method, (iv) an AE test system used for automated determination of evaluation or rejection criteria, and (v) evaluation or rejection criteria determined by the method.

TECHNOLOGICAL BACKGROUND AND STATE OF THE ART

Pressure containers for storing gases tinder an internal pressure are traditionally made of metal, e.g., steel. To achieve adequate safety against failure and/or a permanent imperviousness, certain wall thicknesses must be maintained—depending on the choice of the metal material and the design of the pressure container. One disadvantage of all-metal pressure containers is relatively low storage efficiency (performance factor) based on weight.

A significant weight reduction with at least comparable functionality can be achieved if the pressure container is made not merely of metal but instead partially or entirely of a composite material. Such pressure containers must of course reliably meet the basic requirements, i.e., they must be impervious and must withstand operating stresses (e.g., the internal pressure). So-called type III pressure containers, as well as those of type II, have a metal liner, which essentially assumes the sealing function and to some extent also has a load-bearing function. To ensure adequate mechanical integrity, a composite fiber material (laminate) is used, e.g., made of epoxy resin-impregnated fiber strands (rowings [sic; rovings]) or tapes having a thermoplastic matrix, etc., that are used for complete winding in type III containers and for circumferential winding in type II. In most cases, carbon fibers are used as the fiber components. They have only one-quarter the density of steel but have approximately three times the static tensile strength of normal steel for seamless bottles. Carbon fibers also have a very low susceptibility to fatigue. Alternative options include aramid fibers, glass fibers and in the future there will also be new fibers (such as basalt fibers) or hybrid composites consisting of multiple fibers types. With these types of containers, the liner forms a type of basic structure and may be made of various materials, e.g., steel, aluminum or thermoplastic (type IV pressure container). The advantage of pressure containers made of composite materials lies primarily in the weight reduction, which may amount to up to 70% with comparable pressure containers made of steel with the same filling. Such pressure containers are used, for example, by emergency vehicles, fire departments and in medical areas. Other areas of use include storage devices for natural gas or hydrogen for use in aviation and space travel, hazardous goods shipping and automotive engineering.

Because of their hazard potential filling and shipping of pressure containers are subject to a general prohibition with reservation for issuance of a permit. A permit is issued only after relevant statutory provisions are met. In Europe, these prerequisites for approval include, for example, pressure testing by performing a leakage test on each individual container. No random sample pressure testing is allowed for the applications listed above. These also include various tests on random samples of each lot, including destructive tests.

The object of the present invention is to show a mesas by which the quality testing, acceptance testing or inspection testing of pressure containers made of composite materials can be performed easily and with a high reliability by using acoustic emission testing (AE testing). In particular, acoustic emission testing should be adapted to the needs of industrial manufacturing and inspection of pressure containers and should be compatible with existing manufacturing and inspection routines without any great effort. Furthermore, the method should be usable for optimizing container design and technical safety evaluation of the condition of a container during operation in the sense of heath/safety monitoring or recurring pressure testing.

SUMMARY OF THE INVENTION

A first aspect of the invention that contributes toward solving this problem lies in making available a method for evaluating pressure containers made of composite materials (in particular fiber laminates (FL)) by acoustic emission testing. This method comprises the steps:

(a) determining a sufficient number of internal pressure-dependent acoustic emission characteristics (AE characteristics) of pressure containers from identical production that have been classified as being without defects in predetermined phases of a time-controlled pressure acting upon the pressure container (AE test procedure) with one or more acoustic emission channels (AE channels) using acoustic emission sensors (AE sensors) of a predetermined position (one AE characteristic per AE sensor or AE channel);

(b) defining feature criteria on the basis of the AE characteristics compiled from step (a) and quantification of all AE characteristics from step (a);

(c) statistical analysis of the quantified feature criteria of all AE characteristics from step (b), separated according to feature criteria;

(d) quantitative determination of evaluation criteria or rejection criteria—depending on the goal—for each quality criterion or each desired combination of quality criteria by defining limit values for the feature criteria from step (c);

(e) quantitative determination of the measured values for each feature criterion of each AE channel by analogy with steps (a) and (b) for each of the pressure containers to be evaluated and (f) comparison of the measured values from step (e) with the evaluation criteria and/or rejection, criteria from step (d).

By means of the procedure described here, it is possible for the first time to perform and quantitatively evaluate an AE test for design optimization, manufacturing control or acceptance pressure testing, inspection and constant monitoring during operation on pressure containers made of composite materials. The quasi-non-destructive test method is suitable in particular for integration into industrial development and manufacturing processes and for use in recurrent testing (inspections) or for health/safety monitoring (e.g., in filling operations) on pressure containers. Regardless of the application, this method always includes the identical steps for determining the evaluation criteria and/or rejection criteria on the basis of the feature criteria according to steps (a) through (d), and comparing the individual measurement results according to step (e) on the pressure container to be evaluated with the limit values for the feature criteria from step (d).

AE testing has essentially been known for many years and is used to a significant extent for testing all-metal pressure containers. When used to verify gas pressure tests, it eliminates—in comparison with a conventional water pressure test—the need for cost-intensive and damage-prone dismantling of the pressure containers and drying of the pressure containers after the water pressure test. In addition, the results of AE testing are far more relevant than those of a pure water pressure test with regard, to the actual condition of the pressure container.

Conventional construction material initially exhibits an elastic behavior. With an increase in load and strain exerted on the material, the elastic energy stored in the material increases. On exceeding the limit of elasticity, there may be classic deformation (metals) or brittle fracture (fiber laminates), depending on the toughness of the material. If there is a defect in the elastically strained material, the stresses will concentrate there and cracks may develop, causing a sudden local release of stress in the material. The resulting short-term surge of movement leads to the development of an elastic wave (acoustic emission event) that propagates in the component and can be detected by suitable acoustic emission sensors (AE sensors). AE testing detects and interprets the acoustic events arising from such cracking processes and can at a very early point in time detect, recognize, display and, if necessary, localize incipient macrodamage in the object being tested (see also U.S. Pat. No. 3,545,262 and U.S. Pat. No. 4,577,487).

In conventional AE testing of metal pressure containers, an acoustic emission event is detected by elastic energy released locally and the resulting stress waves. A pressure container can be tested and/or monitored with a relatively small number of AE sensors at fixed positions. Acoustic emission testing allows detection of defects more or less at the moment when the acoustic emission occurs, so it is a real-time test and can therefore be used for early detection of hazards, e.g., even in a conventional pressure test.

It has been found that it is not readily possible to transfer the procedures of AE testing already established for metal pressure containers to pressure containers made of composite materials. An important difference consists of the fact that the nature of the acoustic emission events in the case of composite materials differs greatly from that of all-metal pressure containers because of the use of fiber material and plastics. The deviating microdamage behavior of composite materials usually does not allow analysis and evaluation of the amplitudes/energies of individual events (bursts) as is the practice with conventional AE testing on all-metal pressure containers.

This is essentially due to the high acoustic emission rate that is detected on pressure containers made of composite materials. The inventive approach is to evaluate the "continuous" acoustic emission, which is induced and measured in predetermined phases with time-controlled application of pressure (and/or release of pressure), and to do so on the basis of feature criteria. The values of each feature criterion are compared individually or in combination with the evaluation criteria or rejection criteria, which, as limit values, are characteristic of the AE curve of pressure containers that have been classified as detect-free. In other words, if the individual AE characteristic recorded during AE testing of a pressure container deviates from the AE parent curve (the feature criteria along with ah the respective limit values may be combined in one AE parent curve), i.e., if the tolerances set on the basis of the AE parent curve for the feature criteria are exceeded, then the rejection criterion has been met and it must be assumed that the pressure container was not manufactured in a quality-compliant manner or there has been damage. If multiple rejection criteria are met at the same time, then it must be assumed with an increasing probability that this pressure container is defective and must therefore be rejected.

Pressure containers classified as detect-free by conventional quality control methods are understood to be pressure containers that have been evaluated as being defect-free in the sense of reference containers. Such conventional quality test methods include, for example, the water pressure test with and without volume expansion measurement, matrix analyses and winding protocols. In the ideal case, the properties of the reference containers are subjected to destructive testing for control purposes in AE testing in the sense of design testing.

According to a preferred variant of the method, the pressure container has a metal liner (so-called type II and type III containers) and the AE test procedure comprising step (a) and step (e) in the manufacturing process of the pressure container is performed simultaneously with autofrettage. Autofrettage is a method of increasing the fatigue strength of pressure containers having a metal liner in which by means of a single application of a stretching pressure that is far above the operating pressure, inherent pressure stresses are created in the metal liner in a targeted manner, so that the average tension in the liner is shifted in the direction of the pressure stress range (from a threshold-load to an alternating load) due to the dynamic operating load and, thus, the development of cracks in the liner is delayed.

As an alternative or in addition, the AE test procedure comprising step (a) and step (e) in the manufacturing process of the pressure container may also hike place simultaneously with a final pressure test (product acceptance testing and/or testing before starting operation). Tins variant of the method is recommended in particular for all-composite containers having a nonmetal liner.

The AE test procedure of step (e) may also be performed simultaneously with pressure tests (on prototype containers) during the development process to optimize a pressure container design or a manufacturing method if a basic design has been measured and described according to steps (a) through (c). New findings from step (e) can also be interpreted as new basic values according to step (a) in combination with step (b). The optimization criterion of the minimal total energy in each pressure interval replaces the quantitative specification of upper and lower limits for the evaluation criteria for each feature criterion (for example, the feature criterion (1), which is to be specified in greater detail below, is to be maximized while the other criteria mentioned them are to be minimized).

According to another variant of the method, the AE test procedure consisting of step (a) and thus also step (e) may be performed simultaneously with a pressure test during an inspection test of the pressure container (recurring test; bringing on the market again).

Finally, the AE test procedure from step (e) may be performed during operation (e.g., during the filling operation) of pressure containers having a high hazard potential as a method for technical safety monitoring (health/safety monitoring). The corresponding feature criteria according to steps (a) through (c) and the rejection criteria in the sense of step (d) must be determined during the initial test or other criteria with regard to the level or the progressive increase in feature criteria must be defined in advance.

For all variants and applications, it is essential that the reference group and the pressure container to be evaluated most be tested each time in a manner that is technically comparable in the sense of steps (a) and/or (e) and the feature criteria from the test results of the pressure containers to be evaluated must be compared with the quantitative limit values from step (d).

Preferably in step (b), one or more feature criteria are stipulated that meet the following conditions:

(1) an internal pressure $P_0$ defined as the point of intersection with the pressure axis from linear curve fitting above P*;

(2) a cumulative energy $E_{AE,P*}$, up to an internal pressure P* where P* denotes the pressure level above which there is an almost linear increase in the cumulative energy versus pressure;

(3) an increase in the cumulative energy in a certain standardized pressure interval ($\Delta E_{AE}/\Delta P$) of varying pressure, in particular increasing pressure, whereby the starting point of the pressure interval is derived from P* and the end point of the pressure interval results from the end of the linear increase in energy during the test procedure;

(4) a cumulative energy ($E_{[AE],Pr}$) until the start of a pressure-holding phase of the test procedure;

(5) a cumulative energy ($E_{[AE],Ph}$) during the pressure holding phase of the test procedure; and (6) a strongly progressive or sudden characteristic of the cumulative AE energy in certain pressure intervals, making it difficult or even impossible to determine values for criteria (1), (2) and (3).

The absolute values of the aforementioned feature criteria depend on the AE measurement technique used (type of sensor and frequency filtering), the settings of the AE measurement parameters, the rate of application of pressure and/or reduction in pressure and the temperature of the pressure container. They have proven successful especially. In the autofrettage process with type III pressure containers, but they are also universally relevant for other applications. An AE performance characterised by feature (6) in pressure testing points to inconsistent manufacturing results in containers in autofrettage testing or pressure acceptance testing but also point to failure-critical damage states in an inspection test or in health/safety monitoring.

A second aspect of the present invention that contributes toward solving this problem lies in providing a data medium or circuit that contains the feature criteria for the original step (a) with step (b) obtained according to the preceding method and/or evaluation criteria and rejection criteria from step (d) for comparable steps (a) with (b). Logically, each measurement from step (a) and/or its analysis after step (b) should be available in the data medium—regardless of whether it was determined with regard to the reference group or in product measurements—in order to be able to verify steps (c) and (d) and thus also the limit values of the rejection criteria and/or evaluation criteria at regular intervals, e.g., with regard to the relevance of the random sample. Such a circuit/data medium can supply the aforementioned content as hardware or software, and in the case of the data medium, it may also be embodied in the form of a CD-ROM or hard drive, for example.

A third aspect of the present invention that contributes toward solving this problem lies in providing an AE test system for testing pressure containers made of composite materials. The AE test system comprises:

(i) one or more AE channels consisting of AE sensors in a predetermined position, a signal amplifier and signal recording unit (measurement card) for acquisition of the acoustic emission, as well as parameter channels for determination of the internal pressure and, if necessary, the temperature of the container during an AE test procedure;

(ii) a data medium/circuit according to the embodiment defined above; and (iii) an analyzer unit (e.g., computer) that is connected at the input end to the data medium/circuit and the AE channels and in which the relevant evaluation criteria and/or rejection criteria are compared with the acoustic emission detected on the present pressure container.

If possible, the AE test system serves to provide an automatic evaluation of the rejection criteria with clear recommendations for action, e.g., "accepted" or "rejected,"

A fourth aspect of the present invention that contributes toward solving this problem consists of providing an acoustic emission test system for pressure containers made of composite materials, comprising:

(i) one or more AE channels consisting of AE sensor(s) in predetermined position(s), signal amplifier and signal recording unit (measurement card) for acquisition of the acoustic emission, as well as parameter channels for determination of the internal pressure and, if necessary, the temperature of the container during an AE test procedure; and (ii) an analyzer unit that is capable of ascertaining evaluation criteria or rejection criteria according to step (d) of the method described above independently on the basis of predetermined feature criteria and statistical specifications.

The AE lest system serves to provide automated determination of evaluation or rejection criteria.

A fifth aspect of the invention that contributes toward solving this problem lies in providing evaluation or rejection criteria that are obtained according to step (d) of the method described above.

This invention is explained in greater detail below in exemplary embodiments on the basis of the respective drawings, in which.

Figure 1:
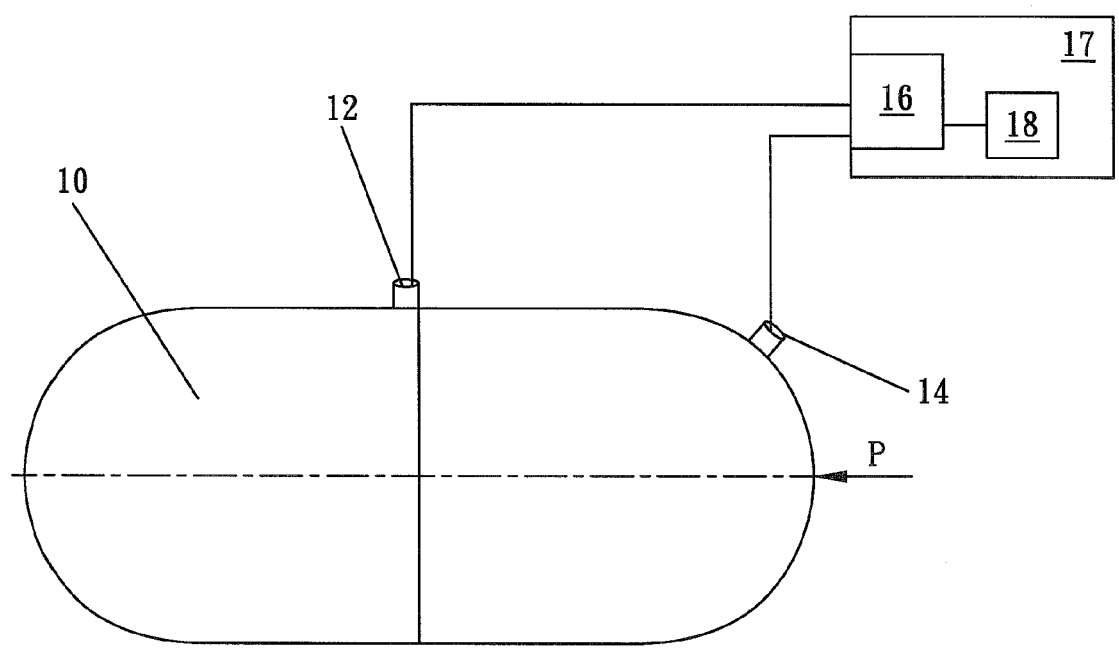
FIG. 1 shows a basic diagram to illustrate an AE test system.

FIG. 1 shows a basic diagram to illustrate an inventive AE test system. Two AE sensors 12, 14 are positioned on the pressure container 10 made of a composite material, namely a first AE sensor 12 positioned centrally in the cylindrical area and a second AE sensor 14 placed on the bottom of the pressure container 10. Depending on the design and geometry of the pressure container 10, other AE sensors may also be arranged on the pressure container 10. The AE sensors 12, 14 are connected at the outlet end by signal lines to a signal recording and analyzing unit 16 of an AE test system 17, which is in turn connected at the input end to a memory means 18 so that the data stored in the memory means 18 can be input. During the test procedure, the pressure container 10 is acted upon from the inside by a pressure P, in particular by introducing a test gas.

The AE sensors 12, 14 are connected by a suitable acoustic coupling means and a mechanical holder. When used in mass production and mass testing of pressure containers 10, the AE sensors 12, 14 can be connected mechanically automatically by a manipulator to coupling means via a spring strap for constant pressing forces and rapid wetting [Translator's note; "Wetting" (Benetzung) appears to be a typographical error for "use" (Benutzung).]. AE sensors 12, 14 generate the acoustic emission signals during the pressure loading and relay the signals to the signal recording and analyzing unit 16—optionally by way of an internal or external preamplifier. Features that represent the intensity of the signals (e.g., energy, counts, amplitude) and the arrival time of the hits are extracted from the transmitted signal. In the case when a "continuous" acoustic emission occurs and a hit-base signal analysis is impossible, the AE signal energy is analyzed based on time. At the same time, the internal pressure P and optionally the temperature of the pressure container 10 are measured as external parameters by the AE test system 17. The data thus acquired are summarized as acoustic emission data record. There follows an analysis of the AE signal energy as a function of the test pressure in analyzer unit 16.

A pressure container 10 having a metal liner, e.g., made of aluminum and an outer laminate, e.g., made of coiled carbon fibers embedded in epoxy resin, is usually subjected to an autofrettage in the manufacturing process. In doing so, a stretching pressure that is below the operating pressure is introduced here. During this manufacturing step, the inventive quality control may take place simultaneously. The phase of the autofrettage process, which is defined by the rate of pressure increase, the maximum pressure and the pressure holding time, is preferably used for quality control. For quality control, it is now necessary to stipulate selection criteria for the autofrettage process.

To do so, first a statistically sufficient number of AE characteristics of pressure containers of the same design that have been classified as defect-free is recorded using the measurement arrangement outline above. The determination is performed in predetermined phases of pressure acting on the pressure containers. In concrete terms its the present example, one phase of the pressure increase is detected in the autofrettage process and a certain interval of time of pressure holding is determined during the autofrettage process. In the present case, it has been found that statistically satisfactory results am obtained by measuring 7 to 13 pressure containers as a reference for the ten selection criteria (five per AE channel) to be described in greater detail below. The number of pressure containers is to be selected in principle, so that the selection criterion has a convergence tendency and the results with regard to the mean and standard deviation may be regarded as statistically certain. For each AE channel the AE characteristics are plotted separately.

Figure 2:
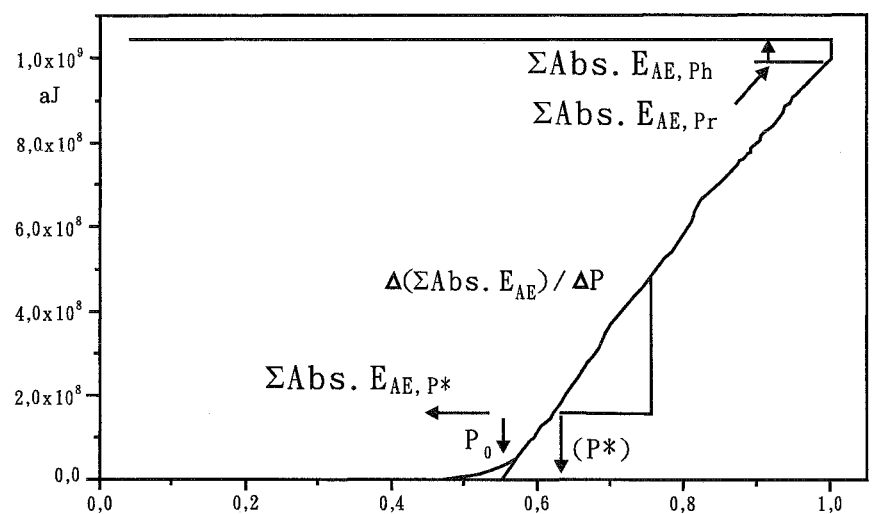
FIG. 2 shows an AE parent curve determined for the autofrettage process.

By statistical analysts of the AE characteristics assigned to each AE channel, standardized and averaged carves of the acoustic emission characteristic whose standard deviations correspond to the respective tolerance limits are obtained. FIG. 2 shows such an AE parent curve from the autofrettage process for AE channel 12 (a corresponding AE parent curve can also be created for the second AE channel 14).

In the next step, the values of the feature criteria are to be ascertained for the parameterization of the AE characteristic of pressure containers classified as defect-free (each based on the AE parent curve of an AE channel). Five such feature criteria cats be derived from FIG. 2.

By linear curve fitting of the AE parent curve to the function $y=A+B*x$ in the pressure range of interest, where $y=\Sigma$ Abs. $E_{AE}$ (y axis: detected cumulative acoustic, emission energy on the first AE channel 12) and $x=P$ (x axis: absolute autofrettage pressure—shown as standardized for reasons of confidentiality in the present example), the feature criteria can be described, as follows:

(1) $P_0=A/B$ (2) $E_{AE,P*}=\Sigma Abs, E_{AE}$ at $P*$ (3) $\Delta(\Sigma Abs, E_{AE})/\Delta P$ (4) $\Sigma$ Abs, $E_{AE,Pr}$ (until the start of the pressure holding phase of the autofrettage process)

(5) $\Sigma$ Abs, $E_{AE,Ph}$ (during the pressure holding phase in the autofrettage process).

Instead of the so-called "absolute" energy (Abs, $E_{AE}$), other methods may also be used to calculate the AE signal energy. The aforementioned feature criteria are fixed. The critical values of the individual feature criteria or of their combination that are combined to form one or more rejection, criteria depend on the design type and geometry of the pressure container, the location of the AE sensors or the conditions prevailing during the test. The individual rejection criteria in the sense of the upper and lower limit values can be defined in the concrete individual case with a maximum of accuracy and a minimum of rejection errors on the basis of pressure containers having different relevant reference errors. The type and extent of reference errors are to be selected so that frequent defects in production (e.g., in matrix mixing, degree of matrix hardening, fiber content, wall thickness or layer structure) are covered. In determining the rejection criteria, those skilled in the art will be able to orient themselves on the exemplary embodiment and will be able to verify corresponding deviations from the design model of the pressure container, the position of the AE sensors and the conditions prevailing during the testing procedure, and they can do so with only a few experiments.

Table 1 shows as an example of the rejection criteria upper and lower threshold values (tolerance limits, limit values) that can be defined on the basis of the stated means and standard deviations, taking into account a set defect probability. Position A relates to the first AE sensor to channel 12 from FIG. 1 and position B is based on the second AE sensor to channel 14 from FIG. 1.

TABLE 1

| Feature criterion | | Unit | Mean | Standard deviation | Lower threshold | Upper threshold | Probability |
|---|---|---|---|---|---|---|---|
| A | 1 | bar | 267 | 8.8 | 2.53E+02 | 2.81E+02 | 5.000% |
|   | 2 | aJ | 2.67E+08 | 1.32E+08 | 4.99E+07 | 4.85E+08 | 5.000% |
|   | 3 | aJ/bar | 9.18E+06 | 1.91E+06 | 6.73E+06 | 1.16E+07 | 10.000% |
|   | 4 | aJ | 1.66E+09 | 4.31E+08 | 6.56E+08 | 2.66E+09 | 1.000% |
|   | 5 | aJ | 6.86E+07 | 2.07E+07 | 2.05E+07 | 1.17E+08 | 1.000% |
| B | 1 | bar | 270 | 8.4 | 2.50E+02 | 2.90E+02 | 1.000% |
|   | 2 | aJ | 1.53E+08 | 5.34E+07 | 6.53E+07 | 2.41E+08 | 5.000% |
|   | 3 | aJ/bar | 5.77E+06 | 7.01E+05 | 4.62E+06 | 6.92E+06 | 5.000% |

TABLE 1-continued

| Feature criterion | Unit | Mean | Standard deviation | Lower threshold | Upper threshold | Probability |
|---|---|---|---|---|---|---|
| 4 | aJ | 9.82E+08 | 1.27E+08 | 6.87E+08 | 1.28E+09 | 1.000% |
| 5 | aJ | 1.16E+08 | 3.17E+07 | 6.43E+07 | 1.69E+08 | 5.000% |

The threshold values given in the table are to be fixed separately for each feature criterion of the AE sensor positions for channels 12, 14 in the sense of a tolerance range. First a consideration of the allowed failure range (probability) that can be tolerated as an erroneous rejection and the reliability required for detecting relevant defects may be considered first. Then, for each AE sensor, specific tolerance ranges (upper and lower thresholds) can be determined on the basis of a relevant distribution for this feature criterion (e.g., standard distribution, Weibull distribution).

Individual rejection criteria may optionally be linked together. For example, it has proven advantageous in the present case if a display of rejection occurs only when at least two of the ten feature criteria of the two AE sensors for the channels 12, 14 are outside of the tolerance ranges. A renewed adjustment of the tolerance values may optionally be necessary in defining such links.

In the ideal case, the functionality of optimization of the rejection criteria is stored and/or programmed according to the definition of the competing boundary conditions of accuracy and erroneous rejection in the technique used (memory unit/circuit 18).

After creation of the AE parent curve and/or defining the rejection criteria plus tolerances, they are stored in the suitable data medium/circuit 18 (FIG. 1). The analysis unit 16 retrieves the stored selection criteria and compares them with the characteristic of the acoustic emission detected from the test object. There is an evaluation of the manufacturing quality of the pressure container to be tested by comparing the individual AE curve with the allowed tolerances (upper and lower threshold of the tolerance range) of individual or lengths rejection criteria with respect to the AE parent curve.

Figure 3:
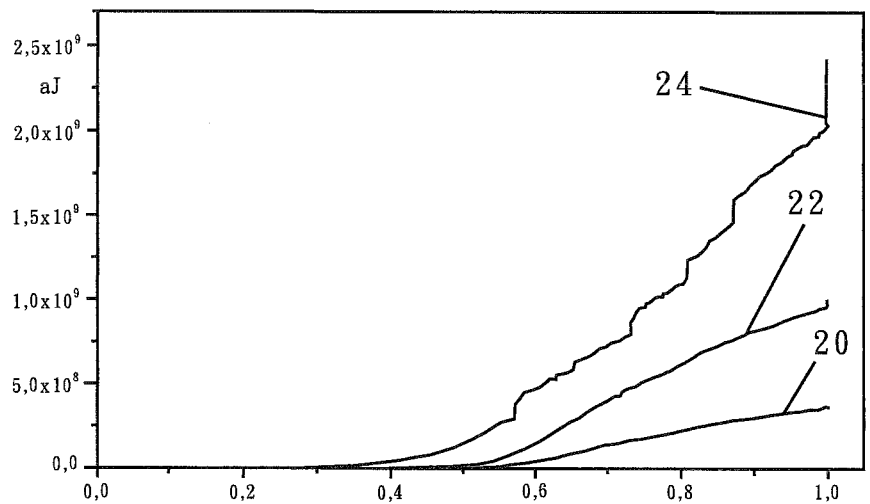
FIG. 3 shows test results on pressure containers with various manufacturing defects.

FIG. 3 shows examples of test results of pressure containers that were recorded in the course of an autofrettage process. Curve 20 corresponds to the AE curve of a pressure container classified as defect-free. Curves 22 and 24 show the individual AE curves of two pressure containers with different manufacturing defects. By comparison with the AE characteristics of pressure containers with reference defects in combination with the position of the AE sensor used, information about the nature of the defect can also be derived from the AE characteristics of the curves 22, 24. If necessary, the results thus obtained can be used for optimizing the pressure container design and the manufacturing method.

The procedure described above, which is tailored specifically to the autofrettage process, can also be applied similarly to the final pressure testing of pressure containers made of composite materials at the end of the manufacturing process. In defining the rejection criteria and designing the AE test system, those skilled in the art can rely on the exemplary embodiment described above.

Likewise, such a defect analysis can also be performed following the inspection of pressure containers made of composite materials, e.g., as an accompanying test with a recurring pressure test that it is prescribed as obligatory.

It is also possible to apply such a defect analysis to the health/safety monitoring of pressure containers made of a composite material using AE sensors attached temporarily to the container during the test procedure or sensors installed permanently, e.g., film-like or fiber-like sensitive AE elements/sensors laminated into or glued on the container.

The invention claimed is:

1. A method for evaluating pressure containers made of composite materials by means of acoustic emission testing, comprising the steps:
    (a) determining a sufficient number of internal pressure-dependent acoustic emission characteristics (AE characteristics) of pressure containers from identical production that have been classified as being without defects in predetermined phases of a time-controlled pressure acting upon the pressure container (AE test procedure) with one or more acoustic emission channels (AE channels) using acoustic emission sensors (AE sensors) of a predetermined position (one AE characteristic per AE sensor or AE channel);
    (b) defining feature criteria on the basis of the AE characteristics compiled from step (a) and quantification of all AE characteristics from step (a);
    (c) statistical analysis of the quantified feature criteria of all AE characteristics from step (b), separated according to feature criteria;
    (d) quantitative determination of evaluation criteria or rejection criteria—depending on the goal—for each quality criterion or each desired combination of quality criteria by defining limit values for the feature criteria from step (c);
    (e) quantitative determination of the measured values for each feature criterion of each AE channel by analogy with steps (a) and (b) for each of the pressure containers to be evaluated; and
    (f) comparison of the measured values front step (e) with the evaluation criteria and/or rejection criteria from step (d).

2. A method according to claim 1, wherein the pressure container has a metal liner and the AE test procedure of step (a) and/or (e) is performed during the manufacturing process of the pressure container simultaneously with autofrettage.

3. A method according to claim 1, wherein the AE test procedure of step (a) and/or (e) is performed in the manufacturing process of the pressure container simultaneously with product acceptance testing and/or testing before initial operation (initial pressure test), in particular in the case of all-composite containers.

4. A method according to claim 1, wherein the AE test procedure of step (a) and/or (e) is performed during a recurring test/inspection simultaneously with a pressure test.

5. A method according to claim 1, wherein to optimize a pressure container design and/or a manufacturing method, the AE test procedure of step (a) and/or (e) is performed simultaneously with a pressure test in the development process.

6. A method according to claim 1, wherein for technical safety monitoring (health/safety monitoring) of pressure containers with a high hazard potential, the AE test procedure of step (a) and/or (e) is performed during operation (e.g., in the filling operation).

7. A data medium or circuit containing feature criteria, evaluation criteria or rejection criteria determined according to steps (a) through (d) of a method according to any one of claims 1 through 6.

8. An acoustic emission test system for pressure containers of a composite material comprising:
   (i) one or more AE channels consisting of AE sensors of a predetermined position, signal amplifiers and signal recording unit (measurement card) for detecting the acoustic emission and parameter channels for detecting the internal pressure and, if necessary, the temperature of the pressure container during the AE test procedure;
   (ii) a data medium or circuit according to claim 7; and
   (iii) an analyzer unit connected at the input end to the data medium/circuit and the AE channels and in which the relevant evaluation and rejection criteria are compared with the acoustic emission detected on the present pressure container.

9. An acoustic emission test system for pressure containers made of a composite material, comprising:
   (i) one or more AE channels consisting of AE sensors of a predetermined position, signal amplifiers and signal recording unit (measurement card) for detecting the acoustic emission and parameter channels for detecting the internal pressure and, if necessary, the temperature of the pressure container during the AE test procedure; and
   (ii) an analyzer unit that is automatically capable of determining evaluation or rejection criteria according to step (d) of the method according to claim 1.

10. An evaluation criteria or rejection criteria obtained by a method according to step (d) of claim 1.

* * * * *